US012514736B2

(12) United States Patent
Ahmadi et al.

(10) Patent No.: US 12,514,736 B2
(45) Date of Patent: Jan. 6, 2026

(54) ARM SLING AND STABILIZATION DEVICE

(71) Applicants: Shahryar Ahmadi, Huntington Beach, CA (US); Peter Kurzweil, Newport Beach, CA (US)

(72) Inventors: Shahryar Ahmadi, Huntington Beach, CA (US); Peter Kurzweil, Newport Beach, CA (US)

( * ) Notice: Subject to any disclaimer, the term of this patent is extended or adjusted under 35 U.S.C. 154(b) by 0 days.

(21) Appl. No.: 18/779,773

(22) Filed: Jul. 22, 2024

(65) Prior Publication Data

US 2025/0032302 A1 Jan. 30, 2025

Related U.S. Application Data

(60) Provisional application No. 63/528,518, filed on Jul. 24, 2023.

(51) Int. Cl.
*A61F 5/37* (2006.01)
*A61F 5/30* (2006.01)

(52) U.S. Cl.
CPC .............. *A61F 5/3746* (2013.01); *A61F 5/30* (2013.01)

(58) Field of Classification Search
CPC ........ A61F 5/3746; A61F 5/30; A61F 5/3738; A61F 5/3723; A61F 5/3715; A61F 5/37; A61F 5/00; A61F 5/3753; A61F 5/01
See application file for complete search history.

(56) References Cited

U.S. PATENT DOCUMENTS

2005/0015033 A1* 1/2005 Moore ............... A41D 13/1245 602/4
2010/0152635 A1* 6/2010 Borden ................. A61F 5/3738 602/4

FOREIGN PATENT DOCUMENTS

JP 3107406 U * 2/2005
WO WO-2006124587 A2 * 11/2006 ........... A61F 5/3753

* cited by examiner

*Primary Examiner* — Tarla R Patel
(74) *Attorney, Agent, or Firm* — Hudak, Shunk & Farine Co. LPA

(57) ABSTRACT

The present invention provides a sling which has a vest base including an arm holder that supports the forearm in a desired weight distribution at a desired position and a first and second forearm support assembly which can be used to support the forearm offset from the wearer's body in higher degrees of abduction.

13 Claims, 2 Drawing Sheets

ARM SLING AND STABILIZATION DEVICE

FIELD OF THE INVENTION

This invention relates to slings or braces for the immobilization and stabilization of the shoulder and arm, such as to allow for recuperation of the joints and muscles, and more particularly to an improved patient intuitive design that provides for an improved distribution of the weight of the immobilized joints and thus encourages better patient compliance.

BACKGROUND OF INVENTION

According to the article "Shoulder Surgery Postoperative Immobilization: An International Survey of Shoulder Surgeons" M. Freehill et al, published on-line Feb. 1, 2023 in the Journal Biology over 500,000 surgical procedures are performed on the shoulder joint each year in the United States and the number of shoulder replacements performed each year between 1998 and 2017 increased 5.6-fold, while surgery for rotator cuff tears has increased by approximately 10% each year over the last decade. These authors state that a significant determinant of recovery following shoulder surgery is the prescribed rehabilitation protocol, but they also note that they are a wide spectrum of postoperative rehabilitation protocols following open and arthroscopic procedures. One widely adopted strategy after rotator cuff repair which is believed to improve outcomes after rotator cuff repair involves the optimization and control of the mechanical environment following surgery, with a period of immobilization of from 3 to 6 weeks on average being a widely adopted strategy.

It is optimal to implement a balanced approach between encouraging use of the affected limb and immobilization to protect the shoulder from excessive forces that may damage the tissues or repair constructs and lead to early failure. It is recognized that action to inhibit loss of mobility or function following rehabilitation can lead to permanent functional difficulties, particularly in an aging population. Medical opinions differ as to the duration and amount of immobilization and optimum arm position, and both products and protocols vary, and especially given the number and types of conditions that can be treated using shoulder immobilization. Examples of conditions for which arm or shoulder slings are used include injuries to the shoulder, arm, and wrist, such as sprains, strains, tendinosis, dislocations, tears, fractures; surgeries, (including shoulder, elbow, wrist, clavicular, and rotator cuff to name a few); and comfort following a stroke.

The current conventional slings in the market have a strap that passes around the neck to support the immobilized arm. This structure results in the transfer of the weight of the arm to the neck of the patient. It is very common that the patient complains about neck pain due to the weight of the arm that is transferred to the neck area especially in people with pre-existing cervical spine issues or weakness in the shoulder girdle. This situation often gives rise to non-compliant patients who give up stabilization of the injured arm since they find the current slings to be painful, as well as inconvenient. This can lead to poor outcomes and decreased functional ability in the affected limb.

The sling of the present invention is designed to offset the weight of the arm to the whole body and shoulders versus neck area. The use of this sling is intuitive for the patient, and as comfortable and natural as allowing the arm to rest in well placed pockets in a favorite garment. The affected limb is comfortably cradled in a natural position that allows for a monitored amount of motion while providing for support to the limb, shoulder girdle, and torso. Moreover, it allows for the appearance of a vest or sporting garment which encourages the user to don the sling over a longer period of time without re-enforcing the idea that the user is infirmed. Thus, it provides for easy and comfortable use, does not cause neck pain and encourages improved patient compliance over the full prescribed period of rehabilitation.

SUMMARY OF THE INVENTION

The sling of the present invention includes a base garment or base such as a sleeveless vest which is used to support the immobilized shoulder and arm, and which includes a back portion joined to a right front side and a left front side. The base includes a right arm hole and a left arm hole and an opening for the head and neck of the wearer. Optimally, the right front portion and the left front portion are each joined, such as by sewn shoulder seams or refastenable snaps or hook and loop, to the top of the back portion, and to each other by closure means, such as a zipper, ties, buttons, hook and eyes, snaps, or hook and loop closures. An advantageous neck-opening is a deep V which is cut away from the soft tissue of the neck, which directs the weight of the supported arm away from the neck and cervical spine and onto the upper torso.

At least one side, and preferably both sides of the vest includes an arm holder to allow for use for either of the right side and the left side. The arm holder preferably allows for various positions of the arm. In a first position, the vest includes front and back through holes that allow the forearm to be inserted with the upper arm hanging in line with the torso (i.e., with the axis of the humerus aligned to the coronal plane +/−5°, and the forearm at an angle of 90°+/−15°, and preferably +/−5° to the humeral axis. Advantageously, the vest further includes an interior support or hammock attached at either longitudinal end to the front and back through holes which supports the weight of the forearm and also aids in directing this weight into the base of the vest such that the weight is supported at the chest and even through the back of the vest.

In addition, the vest includes a restraint, which helps to secure the forearm within the interior support and to keep it from backing out. The restraint is adjustable in length and height to permit variations in size and in the positioning of the arm relative in and out of the interior support.

In addition, the sling of the present invention is provided with a forearm support means that allows for the forearm to be position at an offset to the body. Specifically, the support includes a firm, but cushiony block of a length of 10 to 15 inches, and preferably 8 to 10 inches; a width of 3 to 5 inches, and preferably of from 3 to 5 inches; and a height of from 3 to 8 inches, with a cross section of a trapezoid having a top surface that forms an angle of from 30 to 85°, and preferably 60°+/−10°, with the back side of the block. The block can be rectilinear, or can include a curve so as to accommodate the rounded shape of the torso. The back side of the block which is the taller side of the block, includes means to fasten the block to the outside of the base, where cooperating hook and loop is optimal since it allows for adjustment of the placement of the block. Optimally, the base includes mating hook and loop fasteners and a superior flap that has interior hook and loop such that it is secured to the base hook and loop if the forearm support is not used, and to an axillary sling member if it is used. In this case, the sling is supported by the flap on one side, and by the base on the other.

An additional block can be added to the design to lift the arm further into abduction. In this case, the second block has a bottom surface that matches the top surface of the first forearm block and a side surface that abuts the front surface of the first forearm block so that the block is fully supported, and the bottom of the second block has hook and loop fasteners that mate with hook and loop fasteners on the top of the first forearm block.

This vest can be used in several different ways. The first shown in FIG. 1 is just putting the arm through an opening at the side of the vest that works like a tunnel and the arm goes through it. The second option is using it with a block of foam that is illustrated in FIGS. 2-6. This keeps the arm in abduction. In a third option is adding another block of foam shown in FIG. 7 to support the arm in more abduction (somewhere between 60 to 90° of abduction).

DETAILED DESCRIPTION OF THE INVENTION

Figure 1:
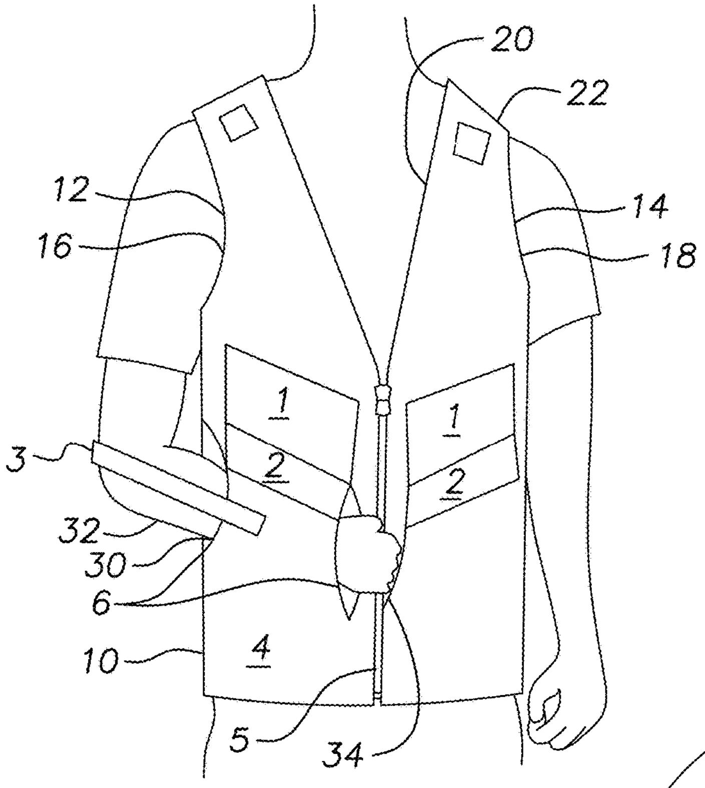
FIG. 1 is a front view of a shoulder sling in accordance with the present invention.
Figure 2:
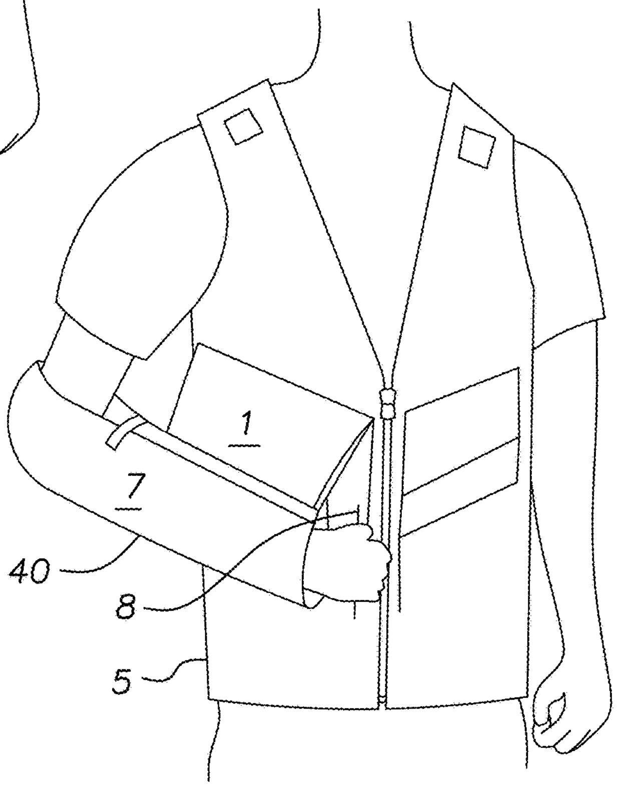
FIG. 2 is an alternate use of the sling of FIG. 1 with a single abduction block.
Figure 3:
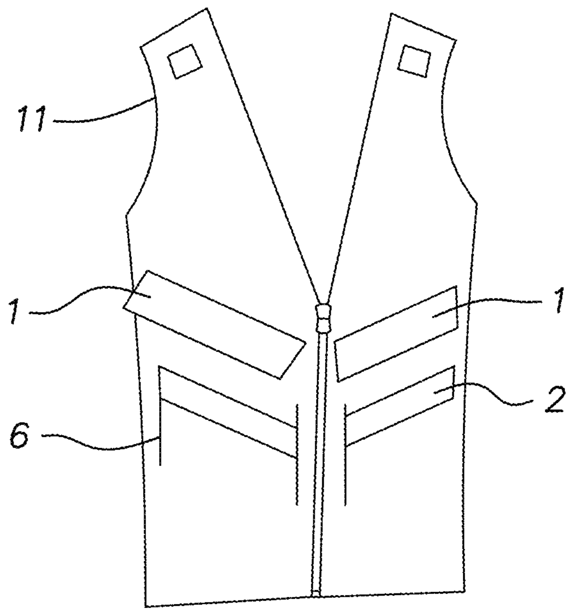
FIG. 3 is a front view of the base vest of FIG. 1 without a wearer.
Figure 4:
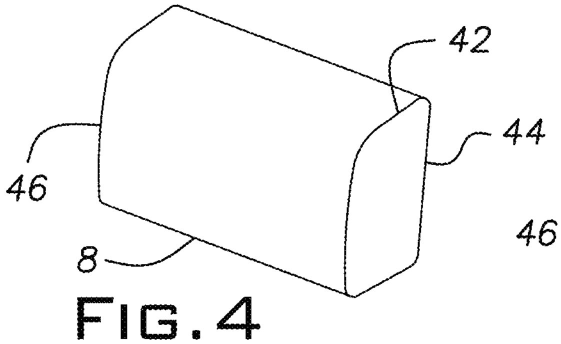
FIG. 4 is a side end view of the offset block of FIG. 2.
Figure 5:
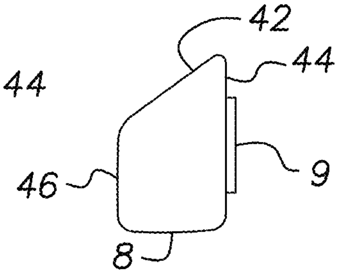
FIG. 5 is an end view of the block of FIG. 4.

As seen in FIG. 1, the sling 10 of the present invention includes a base garment or base 4 such as a sleeveless vest which includes a back portion (not shown) joined to a right front side 12 and a left front side 14. The base includes a right arm hole 16 and a left arm hole 18 and an opening 20 for the head and neck of the wearer. Optimally, the right front portion 12 and the left front portion 14 are each joined, such as by sewn shoulder seams 22 or refastenable snaps or hook and loop, to the top of the back portion, and to each other by closure means, such as a zipper 5, ties, buttons, hook and eyes, snaps, or hook and loop closures. An advantageous neck-opening is a deep V which is cut away from the soft tissue of the neck, which directs the weight of the supported arm away from the neck and cervical spine and onto the upper torso.

There is an arm holder 6 formed in or attached to the vest 4. In this configuration of the sling 10, the arm holder 6 comprises an interior support 30 or hammock attached at either longitudinal end to the front and back through holes 34 in the vest. This interior support 30 supports the weight of the forearm and also aids in directing this weight into the base of the vest such that the weight is supported at the chest and even through the back of the vest. At least one side, and preferably both sides of the vest include the arm holder to allow for use for either of the right side and the left side.

In addition, the vest 4 includes a restraint 3, which helps to secure the forearm within the interior support 30 and to keep it from backing out. The restraint 3 is adjustable in length and height to permit variations in size and in the positioning of the arm relative in and out of the interior support. This adjustability is accomplished by providing a set of hook and loop fasteners on at least one end of the restraint and also on the exterior of the vest 4 so that it can be positioned to allow for a tighter or higher loop as is comfortable and secure.

The arm holder preferably allows for various positions of the arm. In a first position, the vest includes front and back through holes that allow the forearm to be inserted with the upper arm hanging in line with the torso (i.e., with the axis of the humerus aligned to the coronal plane +/−5°, and the forearm at an angle of 90°+/−15°, and preferably +/−5° to the humeral axis.

In addition, the sling of the present invention is provided with a forearm support assembly 40 that allows for the forearm to be positioned at an offset to the body. Specifically, the support assembly 40 includes a firm, but cushiony block 8 configured to support the forearm, and specifically has a length of 10 to 15 inches, and preferably 8 to 10 inches; a width of 3 to 5 inches, and preferably of from 3 to 5 inches; and a height of from 3 to 8 inches, with a cross section of a trapezoid having a top surface 42 that forms an angle of from 30 to 85°, and preferably 60°+/−10°, with the back side 44 of the block 8. The block 8 can be rectilinear or can include a curved surface on the backside 44 so as to accommodate the rounded shape of the torso.

Figure 6:
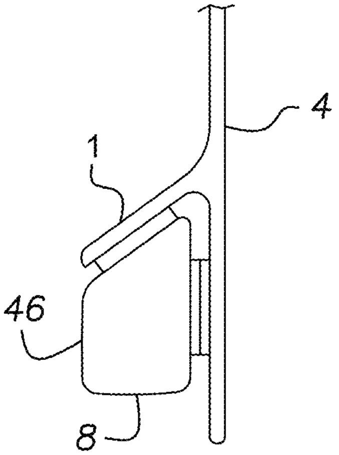
FIG. 6 is an end view of the offset block of FIG. 5 as attached to the base vest.

The back side 44 of the block, which is the taller side of the block, includes means 9 to fasten the block to the outside of the vest 4, where cooperating hook and loop is optimal since it allows for adjustment of the placement of the block. Optimally, the vest 4 includes mating hook and loop fasteners 2 and a superior flap 1 that has interior hook and loop such that it is secured to the vest 4 hook and loop if the forearm support assembly 40 is not used, and to an axillary sling member 7 if it is used. In this case, the sling member 7 is supported by the flap 1 on one side, and by the vest 4 hook and loop on the other. 1. The superior flap 1 is attached to the vest 4 just at its top. A hook section of the hook and loop is positioned underneath it. FIG. 6 shows a cross-section of the sling with the block 8 in position where the flap 1 is attached to the vest at the top and underneath has the hook section of the hook and loop fastener that grabs the abduction pillow or block of the foam 8. A section of hook and loop 2 on the outside of the vest 4 which is the attachment area for the block 8 secures the mating hook and loop on the inside surface of the flap 1 when the block 8 is not in use.

Figure 7:
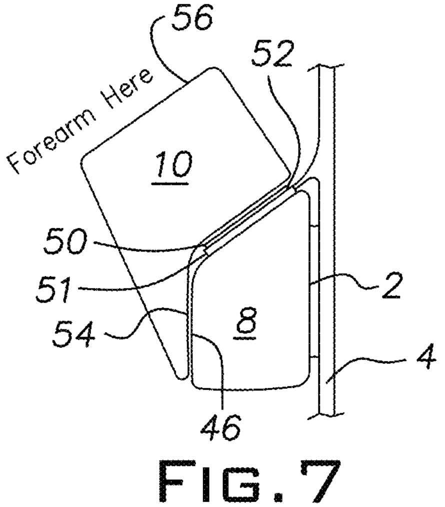
FIG. 7 is an end view of a further alternate use of the sling of FIG. 2 with an additional offset block.

As shown in FIG. 7, an additional block 10 can be added to the design to lift the arm further into abduction. In this case, the second block 10 has a bottom surface 50 corresponds in shape and angle to the top surface 42 of the first forearm block 8 and a side surface 54 that abuts the front surface 42 of the first forearm block 8 so that the second block 10 is fully supported, and the bottom surface 50 of the second block 10 has hook and loop fasteners 52 that mate with hook and loop fasteners 51 on the top surface 42 of the first forearm block 8. In this configuration, the forearm rests on the top surface 56 of the second block 10.

The vest garment of the present invention is preferably made of a material that allows the passage of air and moisture, which is comfortable to wear over time, and which has a certain amount of elastic give to lend resilience to the supportive nature of the sling, such as a mesh fabric, which may include Lycra® or spandex (a generic term for a stretchy fabric), cotton, or polyester. The foam blocks are a firm foam having a cushioning surface, such as memory foam. These materials can be adjusted to provide a price point, and recycled materials can be used.

The sling 10 of the present invention can be used in several different ways. The first shown in FIG. 1 involves putting the arm through an opening at the side of the vest 4 to form the arm support of the sling as it works like a tunnel with the arm resting through it. The second option is using it with a block 8 of foam that is illustrated in FIGS. 2-6. This keeps the arm in abduction. In a third option is adding another block 10 of foam shown in FIG. 7 to support the arm in more abduction (somewhere between 60 to 90° of abduction).

The sling 10 also includes fastening means, such as hook and loop fasteners 11 in both the front and back of the vest at the upper portions near the shoulder seams to allow ice packs to be attached to those loops for cold compress.

What is claimed is:

1. A sling comprising:

a base vest having a back portion joined to a right front side having a right arm opening and a left front side having a left arm opening and a neck opening;

an arm holder formed in or attached to the base vest and comprising a forearm support which forms a tunnel having a front opening and a back opening;

an adjustable restraint which is joined on a first end to the arm holder or the front portion of the base vest and on a second end to the arm holder or to the back portion of the base vest so as to form a closed loop to secure an elbow of a wearer in a position in the arm holder allowing a forearm to be inserted with an upper arm hanging in line with a torso of the wearer with an axis of an upper arm aligned parallel +1-10° to a coronal plane and the forearm at an angle of 90°+/−15° to the axis of the upper arm whereby the weight of the forearm is distributed through the vest to a back and a chest of the wearer;

a flap attached to the base vest to allow the forearm support to be positioned so that the forearm is situated at the angle of 90°+/−15° to the axis of the upper arm and having a section of hook and loop fastener on a surface that opposes a base vest right or left front portion and the base vest including a section of hook and loop fastener facing outward and extending parallel to the flap;

a first foam block with a cross section of a trapezoid and having a top surface joined to a back surface at an angle of from 30 to 85° and configured on the top surface to support the forearm and having a length of 10 to 15 inches, a width of 3 to 5 inches, and a height of from 5 to 8 inches at a front surface and from 5 to 8 inches at the back surface, the back side of the block including a section of hook and loop fastener which is capable of mating with the hook and loop fastener on the flap; and a second foam block having a bottom surface corresponding in shape and angle to the top surface of the first foam block, and a side surface configured to mate with a front surface of the first foam block such that the second foam block is fully supported, and a bottom surface of the second foam block has a section of hook and loop fasteners that mate with a section of hook and loon fasteners on the top surface of the first foam block, wherein the tunnel has a length of 10 to 15 inches and has a front side and a back side which has a section of hook and loop fastener which is capable of mating with the hook and loop fastener on the flap so as to support the tunnel by the flap.

2. The sling as set forth in claim 1, further comprising a right arm holder and a left arm holder.

3. The sling as set forth in claim 1, wherein the restraint is attached to the sling by hook and loop fasteners.

4. The sling as set forth in claim 3, wherein the restraint is a strap having a first end and a second end and which attaches to the tunnel by means of hook and loop fasteners at the first end and at the second end to form a loop on the back opening of the tunnel.

5. The sling as set forth in claim 4, wherein the tunnel is formed in the vest and extends from a first longitudinal end at a front through hole in the vest to a second longitudinal end to a back through hole in the vest.

6. The sling as set forth in claim 1, wherein the first foam block has a top surface that forms an angle of from 60°+/−10° with the back side of the block.

7. The sling as set forth in claim 1, wherein the first foam block has a back side which includes a curved surface to accommodate a rounded shape of a torso of the wearer.

8. A sling comprising:

a base vest having a back portion joined to a right front side having a right arm opening and a left front side having a left arm opening and a neck opening;

an arm holder which is attached to the base vest and comprising a forearm support which forms a tunnel having a front opening and a back opening;

a restraint joined on a first end to the arm holder or the front portion of the base vest and on a second end to the arm holder or to the back portion of the base vest so as to form a closed loop to secure an elbow of a wearer in a position in the arm holder allowing a forearm to be inserted with an upper arm hanging in line with a torso of the wearer with an axis of an upper arm aligned parallel +1-10° to a coronal plane and the forearm at an angle n of 90°+/−15° to the axis of the upper arm whereby the weight of the forearm is distributed through the vest to a back and a chest of the wearer; and a forearm support assembly which includes a foam block with a cross section of a trapezoid and having a top surface joined to a back surface at an angle of from 30 to 850 and configured on the top surface to support the forearm and having a length of 10 to 15 inches, a width of 3 to 5 inches and a height of from 5 to 8 inches at a front surface and from 5 to 8 inches at the back surface, the back side of the block including a section of hook and loop fastener.

9. The sling as set forth in claim 8, wherein the block has a top surface that forms an angle of from 60°+/−10° with the back side of the block.

10. The sling as set forth in claim 9, wherein the block has a back side which includes a curved surface to accommodate a rounded shape of a torso of the wearer.

11. The sling as set forth in claim 8, wherein the forearm support assembly includes a second block having a bottom surface corresponding in shape and angle to the top surface of the foam block, and a side surface is configured to mate with a front surface of the foam block such that the second block is fully supported, and a bottom surface of the second block has a section of hook and loop fasteners that mate with a section of hook and loop fasteners on the top surface of the foam block.

12. The sling as set forth in claim 8, wherein the base vest includes a flap attached to the base vest to allow the forearm holder to be positioned so that the forearm is situated at the angle and having a section of hook and loop fastener on a surface that opposes a base vest right or left front portion and the base vest including a section of hook and loop fastener facing outward and extending parallel to the flap and which is capable of mating with the hook and loop fastener on the back side of the block to secure the block to the vest or with the hook and loop section on the flap.

13. The sling as set forth in claim 8, wherein the forearm support assembly includes a second block having a bottom surface corresponding in shape and angle to the top surface of the foam block, and a side surface is configured to mate with a front surface of the foam block such that the second block is fully supported, and a bottom surface of the second block has a section of hook and loop fasteners that mate with a section of hook and loop fasteners on the top surface of the foam block.

* * * * *